United States Patent [19]
Arndt et al.

[11] Patent Number: 4,908,478
[45] Date of Patent: Mar. 13, 1990

[54] SINGLE-VESSEL PROCESS FOR PREPARING 2-ACETAMINONAPHTHALENE-6-SULFONIC ACID OF HIGH PURITY

[75] Inventors: Otto Arndt, Hofheim am Taunus; Theodor Papenfuhs, Frankfurt am Main, both of Fed. Rep. of Germany

[73] Assignee: Hoechst Aktiengesellschaft, Frankfurt am Main, Fed. Rep. of Germany

[21] Appl. No.: 271,376

[22] Filed: Nov. 10, 1988

Related U.S. Application Data

[63] Continuation of Ser. No. 885,014, Jul. 14, 1986, abandoned.

[30] Foreign Application Priority Data

Oct. 9, 1985 [DE] Fed. Rep. of Germany ....... 3536036

[51] Int. Cl.$^4$ .......................................... C07C 143/60
[52] U.S. Cl. .................................................... 562/55
[58] Field of Search ............... 260/508, 507 R, 512 C; 562/55

[56] References Cited

FOREIGN PATENT DOCUMENTS 0031299 2/1985 European Pat. Off. .
2531281 4/1980 Fed. Rep. of Germany .
436464 10/1935 United Kingdom .

OTHER PUBLICATIONS

Drake, "The Bucherer Reaction" in *Organic Reactions*, vol. 1, John Wiley & Sons, Inc., N.Y., N.Y., 1942, p. 105 ff.
Shine, *Aromatic Rearrangements*, Elsevier Pub., N.Y. (The Bucherer Reaction), 1967, p. 207 ff.
*Angewandte Chemie*, 79, 329–388 (1967).

*Primary Examiner*—Nicky Chan

[57] ABSTRACT

A single-vessel process for preparing 2-acetaminonaphthalene-6-sulfonic acid of high purity by sulfonating 2-hydroxynaphthalene with concentrated sulfuric acid, converting the 2-hydroxynaphthalenesulfonic acid formed with ammonia in the presence of ammonium hydrogensulfite into 2-amino-naphthalene-6-sulfonic acid (Bucherer reaction) and N-acetylating the latter to give 2-acetaminonaphthalene-6-sulfonic acid, which comprises, after diluting the sulfonating melt with water, substantially removing any impurities still present in the resulting aqueous solution of 2-hydroxynaphthalene-6-sulfonic acid, in particular 2-hydroxynaphthalene, by extraction with toluene or xylene and/or clarification using active carbon.

3 Claims, No Drawings

SINGLE-VESSEL PROCESS FOR PREPARING 2-ACETAMINONAPHTHALENE-6-SULFONIC ACID OF HIGH PURITY

This is a continuation of our copending application Ser. No. 06/885,014, filed July 14, 1986, now abandoned.

The invention relates to a single-vessel process for preparing 2-acetaminonaphthalene-6-sulfonic acid or the nonacetylated precursor (2-aminonaphthalene-6-sulfonic-acid) in high purity.

The preparation of 2-aminonaphthalene-6-sulfonic acid with ammonia in the presence of ammonium bisulfite from 2-hydroxynaphthalene-6-sulfonic acid (Bucherer reaction) is known for example from the following references: ORGANIC REACTIONS 1 (1942), N. Drake, page 105; AROMATIC REARRANGEMENTS, H. Shine, Elsevier Publ. Company, 1967, page 207; ANGEWANDTE CHEMIE 79 (1967), No. 8, pages 329–388.

These processes without exception produce a 2-aminonaphthalene-6-sulfonic acid which is contaminated by undesirable side components, in particular by 2-aminonaphthalene.

The present invention thus has for its object to find suitable measures in basically known processes for preparing 2-acetaminonaphthalene-6-sulfonic acid or its nonacetylated precursor (2-aminonaphthalene-6-sulfonic acid) in order to minimize the content of secondary components, in particular 2-aminonaphthalene.

German Auslegeschrift No. 2,531,281 describes a continuous process for preparing inter alia 2-aminonaphthalene-6sulfonic acid, and mentions that aminonaphthalene derivatives appear in the waste gases from the batchwise process. The process was run using the pure alkali metal or ammonium salts of 2-hydroxynaphthalene-6-sulfonic acid; that is, the starting material was not 2-hydroxynaphthalene. Besides, this process is not a single-vessel process.

British Patent No. 436,464 describes a single-vessel process for preparing 2-aminonaphthalene-6-sulfonic acid ("Brönner acid") without, however, considering the appearance of 2-aminonaphthalene.

Finally, European Patent No. 0,031,299 describes a process for preparing 2-aminonaphthalene-1-sulfonic acid ("Tobias acid") from 2-hydroxynaphthalene with the object of preparing this acid with only a very low 2-aminonaphthalene content in a high space-time yield. The aim of producing the 2-aminonaphthalene content in the Tobias acid to trace levels (below 0.1 percent by weight) is achieved in the process by extraction with organic solvents at two points in the process and by switching from alkali metal salts to the more soluble ammonium salts in the intermediate stages. A significant disadvantage of this process is that the extractions take place in two stages. If the chlorinated hydrocarbon which is used as a diluent in the sulfonation of 2-hydroxynaphthalene with chlorosulfonic acid and whose phase is separated from the aqueous product phase after neutralization of the resulting sulfonic acid is included, the number of extraction stages is as high as three.

The first of these extractions is characterized in that it takes place at the stage of the ammonium salt of 2-hydroxynaphthalene-1-sulfonic acid (oxy-Tobias acid ammonium salt solution), i.e. after the sulfonation and neutralization, and that in it 2-hydroxynaphthalene is extracted with chlorinated hydrocarbons, in particular 1,2-dichloroethane, at 70° C. to 75° C. in a countercurrent extraction column. The second extraction is characterized in that it takes place at the stage of the sodium salt of 2-aminonaphthalene-1-sulfonic acid (Tobias acid sodium salt solution), i.e. after the Bucherer reaction, and that in it 2-aminonaphthalene is extracted with toluene or xylene at 70–75° C. in a countercurrent extraction column.

The use of chlorinated hydrocarbons is ecologically very questionable and requires great technical expense and exact product level controls to avoid polluting the environment (waste water, waste air). It is evidently the case here that a single extraction is not enough to achieve the aim of a very low 2-aminonaphthalene content in the Tobias acid.

The purification method used at two different points in the process, namely extraction with different solvents (chlorinated hydrocarbon and toluene/xylene) is too expensive. For example, the individual process measures need to be carried out twice, as for example in using 2 countercurrent extraction columns, 2 phase separations and 2 solvent regenerations. In addition, before the Bucherer reaction it is necessary to remove residues of chlorinated hydrocarbons from the aqueous oxy-Tobias acid ammonium salt solution by strip distillation in vacuo. Attention may be drawn in this context to the possibility of corrosion in the VA stainless steel autoclave on carrying out the Bucherer reaction in the presence of eliminated chloride.

Nothing is said about disposing of the 100% pure 2-aminonaphthalene eventually obtained out of the toluene/xylene extract solutions in the course of solvent regeneration. Combustion of the solvent is said to be too expensive. The regeneration method which is given in the cited European Patent Specification for the chlorinated hydrocarbon for the first extraction, namely regeneration through extraction with water, is unlikely to be adequate in the light of the presence of by-products such as cresols, naphthalene, dimethylphenol, methylnaphthalene, methylnaphthols, phenylnaphthalene, 2,2'-dihydroxy-1,1'-dinaphthyl, polycyclic hydrocarbons (such as for example $C_{18}H_{12}$) or dinaphthyl ether. Regeneration through distillation is therefore likely to be unavoidable.

A further disadvantage of this process is that the sulfonation (with chlorosulfonic acid) is effected in an organic solvent (chlorinated hydrocarbon) and this solvent necessitates a third solvent recycling cycle (extraction with water, dewatering). The process presupposes appreciable solubility of the salts of hydroxy- and aminonaphthalenesulfonic acids in water. The process is not transferable to other isomeric hydroxy- and aminonaphthalenesulfonic acids whose salts are distinctly more sparingly soluble, if they are only present in the form of suspensions and thus prevent phase separation by extraction with organic solvent.

The possibilities given by the references cited were thus not feasible for achieving the stated object of preparing 2-aminonaphthalene-6-sulfonic acid or its N-acetyl derivative with as low as possible a 2-aminonaphthalene content.

The stated object is basically achieved by removing compound which is not reacted in the sulfonation of 2-hydroxynaphthalene, namely unsulfonated 2-hydroxynaphthalene, at suitable points in the preparation process before the Bucherer reaction down to a trace amount of <20 ppm, because 2-aminonaphthalene is formed from the 2-hydroxynaphthalene present by the Bucherer reaction.

The invention relates to a single-vessel process for preparing 2-acetaminonaphthalene-6-sulfonic acid of high purity, i.e. with substantial avoidance of contamination, in particular by 2-aminonaphthalene, in the end product 2-acetylaminonaphthalene-6-sulfonic acid by sulfonating 2-hydroxynaphthalene with concentrated sulfuric acid, converting the resulting 2-hydroxynaphthalenesulfonic acid with ammonia in the presence of ammonium hydrogensulfite into 2-aminonaphthalene-6-sulfonic acid (Bucherer reaction) and acetylating the latter to give 2-acetaminonaphthalene-6-sulfonic acid, which comprises, after diluting the sulfonation melt with water, removing unreacted 2-hydroxynaphthalene still present in the resulting aqueous solution of 2-hydroxynaphthalene-6-sulfonic acid by extraction with toluene or xylene and/or clarification using active carbon to a substantial extent (<20 ppm).

The process according to the invention makes it possible to prepare 2-acetaminonaphthalene-6-sulfonic acid and 2-aminonaphthalene-6-sulfonic acid without having to extract 2-aminonaphthalene, thereby dispensing with this process stage. The isolated 2-aminonaphthalene-6-sulfonic acid (Brönner acid) contains less than 100 ppm of 2-aminonaphthalene. Its aqueous suspensions contain less than 20 ppm of 2-aminonaphthalene.

Contrary to the preconditions derivable from cited EP Patent No. 0,031,299, a single process stage was surprisingly found to be adequate, provided the residual 2-hydroxynaphthalene was after the sulfonation extracted out of the water-diluted, non-neutralized sulfonation mixture and/or adsorbed on active carbon. Aromatic solvents, such as toluene and xylene, i.e. industrially readily manageable solvents, are suitable for the extraction.

It must be regarded as astonishing and surprising that the same effect as described in the cited EP Patent Specification is obtainable with only 1 extraction instead of 2 extractions, evidently as a consequence of the fact that this one extraction occurs at a more suitable point in the process.

The sulfonation of 2-hydroxynaphthalene is carried out with sulfuric acid in the absence of a diluent in accordance for example with BIOS Final Report 986, page 388, British Patent No. 1,341,351 or J. Soc. Chem. Ind. 46, (1927), 25 T-27 T. The evaporation of water at the end of the sulfonation reduces the residual amount of 2-naphthol.

Description of details and preferred embodiments of the process according to the invention:

2-Hydroxynaphthalene is stirred at 86° C. with the same amount by weight of 96% strength sulfuric acid (1.41 moles of $H_2SO_4$ per mole of 2-hydroxynaphthalene) until completely dissolved. The temperature is then raised in steps, namely first to 95° C. and then to 105° C., each being maintained for 30 minutes.

The reaction vessel must be at least 75% full, and the upper inner wall which is not in contact with the reaction melt must likewise be heated in such a way that no sublimate of 2-hydroxynaphthalene forms thereon. The evaporation of water at the end of the sulfonation reduces the residual amount of 2-naphthol (Example 11).

The clear sulfonation melt (1 part by weight) is rapidly poured onto 2.5 parts of cold water with stirring. After complete mixing, the mixture is briefly refluxed. An evaporation of significant amounts of water is to be avoided, since the increase in concentration is accompanied by elimination of 2-hydroxynaphthalene out of the 2-hydroxynaphthalene-6-sulfonic acid and the formation of dinaphthyl ether.

Any small amounts of resins which are formed can if necessary be removed by clarification using filter aids (for example Perlite). The clarification will not remove 2hydroxynaphthalene. The solution contains 0.3 percent by weight of 2-hydroxynaphthalene (corresponding to 2% of theory, based on starting hydroxynaphthalene), or 0.13 percent by weight of 2-hydroxynaphthalene, if water was distilled off at the end of the sulfonation. By clarification using active carbon (60 g of carbon per mole of 2-hydroxynaphthalenesulfonic acid), 90% of the 2-hydroxynaphthalene can be removed (reduction in content from about 4700 ppm to about 400 ppm). The other procedure comprises extracting with toluene or xylene. After 10 extractions at 25° C. with about 20 percent by volume of xylene each time, 2-hydroxynaphthalene is no longer detectable in the aqueous product phase (<5 ppm). Studies have shown that in this case a countercurrent extraction column having about 5 stages is adequate (parts by volume of feed solution: xylene =2:1, extraction yield 99.8%).

A particularly advantageous method is found to be the combination of extraction and treatment with active carbon, whereby a countercurrent extraction column becomes dispensible (Example 11).

The aqueous solution of 2-hydroxynaphthalene-6-sulfonic acid, which also contains about 4% of theory of 2-hydroxynaphthalene-8-sulfonic acid, is brought to pH 7.5 with 25% strength aqueous ammonia while applying external cooling (about 2 moles of $NH_3$ per mole of 2-hydroxynaphthalenesulfonic acid). The suspension then present has successively added to it 40% strength sodium hydrogensulfite solution (about 1.6 mole per mole of 2-hydroxynaphthalenesulfonic acid), 33% strength sodium hydroxide solution (about 1 mole per mole of 2-hydroxynaphthalenesulfonic acid) and 25% strength aqueous ammonia (about 7 moles per mole of 2-hydroxynaphthalenesulfonic acid). The suspension (pH 12.5) is raised to 160° C. in a VA stainless steel stirred autoclave and is subsequently stirred at that temperature for 8 hours. The pressure amounts to about 10 bar. 33% strength sodium hydroxide solution is then injected at 20° C. to 100° C. through a pressure lock under nitrogen pressure in an amount of about 3.5 moles/1 mole, which is followed by stirring at 100° C. for 1 hour (pH 13.3).

The batch is let down at 20° C., and the ammonia is distilled off at normal pressure (102° C.) as completely as possible. The distillate contains no 2-aminonaphthalene (<5 ppm).

The thin suspension (pH 13.4) flows in about 15 minutes with external cooling into initially charged approximately 30% strength hydrochloric acid (about 5-6 moles of HCl per mole of 2-aminonaphthalenesulfonic acid). The thin, pale brown suspension is heated to the boil, and the sulfur dioxide is driven out quantitatively.

The reverse procedure, namely adding the hydrochloric acid to the product solution, is not advisable, since in that case the Bucherer reaction can proceed in the direction of hydrolysis of aminonaphthalenesulfonic acid to hydroxynaphthalenesulfonic acid in particular when the ammonia has not been distilled off to a sufficient extent.

The result obtained is an approximately 6-7 percent by weight strength suspension of 2-aminonaphthalene-6-sulfonic acid (Brönner acid) containing <5 ppm of 2-aminonaphthalene [high performance thin layer chromatography (HPTLC) with quantitative evaluation by scanner]. The pure Brönner acid separated off by filtration is obtained in a yield of 86% of theory, based on the diazotization value of the suspension, or 70% of theory, based on 2-hydroxynaphthalenesulfonic acid, or 69% of theory, based on 2-hydroxynaphthalene. The 2-aminonaphthalene content is <100 ppm (HPTLC, scanner).

The diazotization value of the waste water is 10% of theory, based on the diazotization value of the suspension before filtration (1.5% Brönner acid, 3.3% 2-aminonaphthalene-8-sulfonic acid and 3.1% 2-aminonaphthalene-8-sulfonic acid and 3.1% 2-aminonaphthalenedisulfonic acids; HPTLC, scanner).

The abovementioned alternative purification method through clarification by means of active carbon leads to a suspension of the Brönner acid, which contains about 60 ppm of 2-aminonaphthalene. The Brönner acid isolated therefrom by filtration contains about 1000 ppm of 2-aminonaphthalene.

Accordingly, the isolation of this Brönner acid by filtration is not preferred. However, this leaves the possibility of subjecting the suspension to acetylation, i.e. to convert the small amount of 2-aminonaphthalene present in the suspension into 2-N-acetylaminonaphthalene. Brönner's acid is a precursor of 2-aminonaphth-6-yl-oxyethyl sulfone (CAS No. 52218-35-6, Japanese Offenlegungsschrift No. 73/43,501, European Offenlegungsschrift No. 0,111,288, Example 1). The oxyethyl group is introduced by preparing the sulfochloride of acet-Brönner acid and subsequently reducing the latter to the sulfinic acid with sodium sulfite and oxyethylating with ethylene oxide. For the chlorination to the sulfochloride and the oxyethylation, the amino group must be protected by acetylation.

The acetylation is carried out at 70° C. and pH 7 with acetyl anhydride (1.25 moles per mole of Brönner acid). In the reaction the pH drops to about 3. The result obtained is isomer-free 2-acetaminonaphthalene-6-sulfonic acid (acetyl-Brönner acid) containing about 20 ppm of 2-acetaminonaphthalene (HPLC).

As already mentioned, Brönner's acid is a precursor of 2-aminonaphth-6-yl-oxyethyl sulfone, which is an invaluable precursor for those reactive dyes which become bonded to the cellulose fiber via a vinylsulfonyl group.

Brönner's acid is also a precursor for diazo or coupling components in the preparation of azo dyes.

EXAMPLE 1

(a) A stirred flask is charged with 215 parts of 96% strength sulfuric acid (2.1 moles). With slow stirring, 216 parts of 2-hydroxynaphthalene (1.5 mole) in the form of flakes are added at 30° C. in about 30 minutes.

The temperature is raised to exactly 86° C. (the flask should be immersed as deeply as possible in the heating bath), which is followed by stirring at that temperature for 30 minutes until the complete disappearance of the gradually dissolving sediment of 2-hydroxy-naphthalene. The temperature is then raised to 95° C. in the course of about 1.5 hours, which is followed by stirring at 95° C. for 30 minutes. The temperature is then raised to 105° C. in the course of about 30 minutes. A trace of sublimate of 2-hydroxynaphthalene forms at the uppermost, colder part of the internal surface of the flask.

The highly mobile or slightly viscous melt (105° C.) is then immediately stirred into 840 parts of water, and a temperature of 45° C. becomes established. The portion which remained in the sulfonating flask is taken up once with 150 parts of water and, after vigorous stirring, is likewise mixed in. The sulfonating flask is rinsed with 60 parts of water, which are added to the batch.

The turbid black solution is heated to the reflux point and is refluxed for a maximum of 15 minutes. In general, clarification is not necessary. If it should nonetheless be desired, 6 parts of a filter aid based on a vulcanic mineral (Perlite J 4) are added, the temperatures is reduced to 60° C., and the mixture is filtered through a suction filter. (9 parts of filter residue remained, of which 3 parts are black resin lumps).

The approximately 22% strength product filtrate ($d^{20}$=1.112, amount about 1500 parts) contains 0.30% of 2-hydroxynaphthalene, which corresponds to 4.5 parts of 100%, which corresponds to 2% of theory.

After cooling down to 25° C., the product solution (1350 parts by volume) is stirred up 10 times with 270 parts by volume of m-xylene each time.

The extracted product solution (1450 parts) contains 320 parts of 2-hydroxynaphthalene-6(8)-sulfonic acid (1.42 moles). HPTLC finds <5 ppm of 2-hydroxynaphthalene.

The m-xylene (about 2340 parts) is regenerated by distillation through a column (60 cm of Raschig rings, reflux 5:1, atmospheric pressure, temperature at the top 135–139° C.). The bottom product (5% of the starting amount =120 parts) contains: 2-hydroxynaphthalene (4.5 parts), polycyclic hydrocarbons, dinaphthyl ether and 2,2'-dioxy-1,1'-dinaphthyl.

(b) 1450 parts of the aqueous solution, prepared as described above [Section a)], of 2-hydroxynaphthalene-6(8)-sulfonic acid (320 parts=1.42 moles) are brought with 190 parts of 25% strength aqueous ammonia (2.80 moles) and external cooling to pH 7.5.

The suspension has successively added to it at 5° C. 600 parts of approximately 40% strength sodium hydrogensulfite solution (2.25 moles), 182 parts of 33% strength sodium hydroxide solution (1.50 moles) and finally 750 parts of 25% strength aqueous ammonia (11.0 moles).

The suspension (pH 12.5) is heated in a VA stainless steel stirred autoclave to 160° C. in about 40 minutes and is subsequently stirred at that temperature for 8 hours. The pressure is a constant 10 bar.

630 parts of 33% strength sodium hydroxide solution (5.20 moles) are then injected at 20° C. through a pressure block under nitrogen pressure. The batch is subsequently stirred at 100° C. for 1 hour. The temperature is reduced to 20° C., the pressure is carefully let down and the autoclave is emptied. The autoclave is then rinsed out with 200 parts of water. About 4000 parts of a thin, pale brown suspension of 2-aminonaphthalene-6(8)-sulfonic acid (salt) (pH 13.3) are obtained. About 870 parts of approximately 16% strength aqueous ammonia (about 60% of theory) are then distilled off under atmospheric pressure up to a temperature at the top of 100° C. (bath temperature up to 150° C., cold trap as receiver). The ammonia distillate is slightly turbid due to xylene droplets and, according to HPTLC, contains no 2-aminonaphthalene (<5 ppm). After replenishing with 105 parts of gaseous ammonia to 25%, 940 parts thereof are used for the next batch, about 35 parts are removed from the system.

The suspension (about 3100 parts, pH 13.4) runs in about 15 minutes from a dripping funnel into initially charged, externally cooled 1000 parts of approximately 30% strength hydrochloric acid (8.5 moles). This is followed by heating to the boil and quantitative driving out of sulfur dioxide in about 2 hours by boiling. The sulfur dioxide is trapped in a mixture of 156 parts of water and 255 parts of 33% strength sodium hydroxide solution. This gives 546 parts of a 40% strength sodium hydrogensulfite solution (2.1 moles corresponding to 93% of theory), which are used again for the next batch.

This gives about 4000 parts of a suspension which, according to the diazotization value, contains 6.7% by weight =268 parts of 2-aminonaphthalene-6(8)-sulfonic acid (80% of theory, based on 2-hydroxynaphthalene) with a 2-aminonaphthalene content of 5 ppm (HPTLC, scanner).

The suspension is then cooled down to 60° C. in about 2 hours, and the Brönner acid is isolated by filtration.

This is followed by washing at 25° C. with about 2000 parts of 2% strength hydrochloric acid until the wash filtrate running off is colorless. This gives 230 parts of pure 2-aminonaphthalene-6-sulfonic acid calculated as 100% (Brönner's acid) (=1.03 moles, which corresponds to 86% of theory based on the diazotization value of the suspension or 69% of theory based on 2-hydroxynaphthalene).

The purity (diazotization value) is 96.7%. The product is thin layer chromatographically pure. The 2-aminonaphthalene content is ≦100 ppm (HPTLC, scanner). Also obtained are 3500 parts of mother liquor $d^{20}=1.12$, pH 0.5) with 4.9 parts of 2-aminonaphthalene-6-sulfonic acid corresponding to 1.5% of theory
11.2 parts of 2-aminonaphthalene-8-sulfonic acid corresponding to 3.3% of theory
14 parts of 2-aminonaphthalenedisulfonic acids corresponding to 3.1% of theory
(determined by means of HPTLC, scanner).

The diazotization value of the mother liquor is 0.8% (molecular weight 233, which corresponds to 10% of theory). The 2-aminonaphthalene content is 1 ppm.

Without removing the 2-hydroxynaphthalene from the solution of 2-hydroxynaphthalene-6-sulfonic acid by extraction with toluene or xylene the result obtained would be a 2-aminonaphthalene-6-sulfonic acid which contains about 1.9 percent by weight of 2-aminonaphthalene.

EXAMPLE 2

(a) Example 1 is repeated, except that the solution of the aqueous 2-hydroxynaphthalenesulfonc acid obtained is extracted with toluene instead of xylene, affording about 4200 parts of a suspension which, according to the diazotization value, contains 6.4%, or 267 parts, of 2-aminonaphthalene-6(8)-sulfonic acid. The 2-aminonaphthalene content is 5 ppm (HPTLC, scanner).

(b) The suspension thus obtained [1.20 moles of 2-amino- naphthalene-6(8)-sulfonic acid, pH 0.8] is brought at 70° C. with 245 parts of 33% strength sodium hydroxide solution to pH 7.0 and has added to it 155 parts of acetic anhydride (1.5 moles) in the course of 15 minutes, during which the pH decreases to 3.0 and the Brönner acid goes into solution. The acetylation is quantitative. Salting out gives 289 parts of 2-acetaminonaphthalene-6-sulfonic acid calculated at 100% (1.09 moles which corresponds to 73% of theory based on 2hydroxynaphthalene) having a purity of about 70% (diazotization value after hydrolysis, molecular weight 265.3).

The 2-acetaminonaphthalene content is 100 ppm (HPLC).

The combined mother liquors and wash filtrates (about 4400 parts) contain about 0.3 part of acetaminonaphthalene corresponding to about 70 ppm.

EXAMPLE 3

Example 1 (a) is repeated, except that the extraction is carried out with a countercurrent extraction column having 5 theoretical stages. Volume ratio feed solution (solution of 2-hydroxynaphthalene-6(8)-sulfonic acid): m-xylene =2:1.

The 2-hydroxynaphthalene content in the raffinate (2-hydroxynaphthalene-6-(8)-sulfonic acid solution) is 6 ppm, and the 2-hydroxynaphthalene extraction yield is 99.5%.

EXAMPLE 4

Example 2 (b) is repeated, except that a Brönner acid suspension as obtained in Example 1 (b) is used, affording a 2-acetaminonaphthalene-6-sulfonic acid having a purity of about 70%.

The 2-acetaminonaphthalene content is 23 ppm (HPLC).

The combined mother liquors and wash filtrates (about 4700 parts) contain about 0.1 part of 2-acetaminonaphthalene corresponding to about 28 ppm.

EXAMPLE 5

An approximately 22% strength aqueous 2-hydroxynaphthalenesulfonic acids solution (1500 parts) prepared as described in Example 1(a) contains about 0.40% of 2-hydroxynaphthalene (6.0 parts, calculated at 100%).

The solution is stirred at 60° C. together with 90 parts of active carbon powder for 3 hours and filtered hot with suction. This is followed by washing with 90 parts of water. The result obtained is 1410 parts of product filtrate containing 0.04% of 2-hydroxynaphthalene (0.56 part, calculated as 100%) and 307 parts of 2-hydroxynaphthalenesulfonic acid (1.37 moles).

The carbon retains 5.4 parts of 2-hydroxynaphthalene (90% of the original amount) and 30 parts of 2-hydroxynaphthalenesulfonic acid (0.13 mole, corresponding to about 9% of theory). If 60 parts of active carbon powder are used, 83% of the original amount of 2-hydroxynaphthalene (corresponding to 5 parts) is retained.

Example 6

1410 parts of aqueous 2-hydroxynaphthalene-6(8)-sulfonic acid (containing 307 parts=1.37 moles), prepared as described in Example 5, are converted in the manner described in Example 1 (b) into 2-aminonaphthalene-6-sulfonic acid.

This gives about 4150 parts of a suspension which according to the diazotization value contains 6.0%, corresponding to 249 parts, of 2-aminonaphthalene-6(8)-sulfonic acid (1.11 moles).

The 2-aminonaphthane content is 60 ppm.

Unlike Example 1 (b), in this instance 2-aminonaphthalene is also found in the ammonia distillate (140 ppm).

EXAMPLE 7

The suspension obtained in Example 6, containing 1.11 moles of 2-aminonaphthalene-6(8)-sulfonic acid (pH =1.0), is converted in the manner of Example 2 b) into 2-acetaminonaphthalene-6-sulfonic acid. Salting out gives 282 parts of 2-acetaminonaphthalene-6-sulfonic acid calculated as 100% (1.06 moles corresponding to 71% of theory, based on 2-hydroxynaphthalene, or 77% of theory, based on 2-hydroxynaphthalenesulfonic acid, or 96% of theory, based on 2-aminonaphthalene-6(8)-sulfonic acid) with a purity of 88% (from acetyl determination). The 2-acetaminonaphthalene content is 965 ppm (HPLC).

The combined mother liquors and wash filtrates (6250 parts) contain about 0.2 part of 2-acetaminonaphthalene corresponding to about 30 ppm.

EXAMPLE 8

A sulfonation melt prepared as described in Example 1 (a) is taken up in 1050 parts of water (1482 parts) and after heating to the reflux point is cooled down to 35° C. It contains about 0.21% of 2-hydroxynaphthalene (3.1 parts).

180 parts of 33% sodium hydroxide solution (1.50 moles) are added. The pH value is then 0.4. To the thin, whitish gray suspension are then also added 74 parts of 25% strength aqueous ammonia (1.08 moles) (the pH value is subsequently 3.0).

The whitish gray suspension, which is thin at 50° C., is heated to 95° C.. At 88° C. the salt mixture goes completely into solution. 60 parts of active carbon powder are then added, which is followed by stirring at 95° C. for about 45 minutes. The carbon is then filtered off under nitrogen pressure on a jacketed suction filter heated to 95° C. with steam passing through the jacket.

The product filtrate (1516 parts) has a pH value of 7.5. It contains 0.06% of 2-hydroxynaphthalene, corresponding to 0.91 part.

0% of the residual 2-hydroxynaphthalene was adsorbed. The filter residue after drying at 25° C. is 114 parts. Its sulfate ash is 7.0%. The 2-hydroxynaphthalene content is 1.8% corresponding to 2.1 parts, and the 2-hydroxynaphthalenesulfonic acid 25 parts, corresponding to 7% of theory (titration of naphtholic hydroxyl).

The adsorption of 2-hydroxynaphthalene from the salt solution is thus distinctly lower than from the sulfonic acid solution (compare Example 5).

EXAMPLE 9

1516 parts of aqueous 2-hydroxynaphthalene-6(8)-sulfonic acid obtained as described in Example 8 (pH 7.5) are diluted with 500 parts of water and cooled down to 5° C. To this are added 600 parts of approximately 40% strength sodium hydrogensulfite solution and 775 parts of 25% strength ammonia (pH 10.6).

The suspension is transferred into a VA stainless steel stirred autoclave and is converted into 2-aminonaphthalene-6-sulfonic acid as described in Example 1(b).

This gives about 4380 parts of a suspension which according to the diazotization value contains 5.55% corresponding to 243 parts (1.09 moles) of 2-aminonaphthalene-6(8)sulfonic acid, corresponding to 73% of theory based on 2-hydroxynaphthalene. The 2-aminonaphthalene content is 83 ppm (compare Example 6).

If this value is based on the 243 parts of Brönner acid, it is found that this product, if isolated by filtration, contains 1500 ppm of 1-aminonaphthalene, which is undesirably high.

EXAMPLE 10

The suspension obtained in Example 9 [containing 1.09 moles of 2-aminonaphthalene-6(8)-sulfonic acid, pH value 0.9] is converted into 2-acetaminonaphthalene-6-sulfonic acid as described in Example 2 (b).

Salting out gives 247 parts of 2-acetaminonaphthalene-6-sulfonic acid calculated at 100% (0.93 mole corresponding to 86% of theory, based on 2-aminonaphthalene-6(8)sulfonic acid (having a purity of 74%, determined from the diazotization value after hydrolysis).

The 2-acetaminonaphthalene content is 2120 ppm (HPLC).

The combined mother liquors and wash filtrates (5542 parts) contain 0.4 part of 2-acetaminonaphthalene corresponding to about 70 ppm.

EXAMPLE 11

(a) A stirred flask is charged with 215 parts of 96% strength sulfuric acid (2.1 moles). With slow stirring, 216 parts of 2-hydroxynaphthalene (1.5 mole) in the form of flakes are added at 30° C. in about 30 minutes. The temperature is raised to exactly 86° C. (the flask should be immersed as deeply as possible in the heating bath), which is followed by stirring at that temperature for 30 minutes until the complete disappearance of the gradually dissolving sediment of 2-naphthol. The temperature is then raised to 95° C. in the course of about 1.5 hours. The flask is evacuated to 1-1.5 mbar and the batch degassed at 95° C. The temperature is then raised to 100° C. in the course of 20 minutes for the subsequent distilling off of water, and this temperature is maintained until distillation subsides, whereupon it is raised to 106° C. in the course of 20 minutes. A trace of sublimate of 2-hydroxynaphthalene forms at the uppermost, colder part of the internal surface of the flask.

The amount of distilled-off water in the receiver and cold trap is 12 parts.

The highly mobile to slightly viscous melt (106° C.) is then immediately stirred into 840 parts of water, and a temperature of 45° C. becomes established. The portion remaining in the sulfonating flask is taken up once with 150 parts of water and, after vigorous stirring, is likewise admixed.

The sulfonating flask is rinsed out with 60 parts of water which are added to the batch. The turbid, black solution is then heated to the reflux point and refluxed for no more than 15 minutes.

The approximately 22% strength product solution ($d^{20}=1.115$, amount about 1475 parts) contains 0.13% of 2hydroxynaphthalene, corresponding to 1.92 parts of 100%, corresponding to 0.9% of theory (HPTLC). Compared with the result of Example 1, distilling off water thus has the effect of additionally converting 2.6 parts (1.2% of theory) of 2-naphthol.

The product solution is stirred up once at 80° C. with 260 parts of m-xylene. The extracted product solution (1464 parts) contains 323 parts of 2-hydroxynaphthalene-6(8)-sulfonic acid (1.44 moles) and 0.07% of 2-hydroxynaphthalene, corresponding to 1.03 parts of 100%, corresponding to 0.5% of theory (HPTLC).

The product solution is stirred up twice in succession at 50°C with 30 parts of active carbon powder each time, and clarified. The filter residue is washed with 300 parts of water in each case. The 2-naphthol content decreases in the course of the treatment to 62 ppm (0.105 part, 0.05% of theory) in the 1st filtrate (1700 parts) or to 5 ppm (0.01 part) in the 2nd filtrate (2000 parts).

After the reverse procedure (first clarify with carbon, then stir up once with m-xylene), the 2-naphthol content is still 100 ppm (corresponding to 0.17 part).

(b) 2000 parts of the aqueous 2-hydroxynaphthalene-6(8)sulfonic acid solution prepared as described above (section a) (325 parts =1.45 moles) are brought with 196 parts of 25% strength aqueous ammonia (2.88 moles) and external cooling to pH 7.8. The suspension then has added to it in succession at 5° C. 620 parts of approximately 40% strength sodium hydrogensulfite solution (2.35 moles), 188 parts of 33% strength sodium hydroxide solution (1.55 moles) and finally 775 parts of 25% strength aqueous ammonia (11.38 moles).

The suspension (pH 12.6) is heated in a VA stainless steel stirred autoclave to 160° C. in about 40 minutes and is subsequently stirred at that temperature for 8 hours. The pressure is a constant 9-10 bar approximate.

651 parts of 33% strength sodium hydroxide solution (5.37 moles) are then injected at 20° C. under nitrogen pressure through a pressure lock. The batch is subsequently stirred at 100° C. for 1 hour. This is followed by cooling down to 20° C., carefully letting down the pressure and emptying the autoclave. This is followed by rinsing with 200 parts of water. The result obtained is 4460 parts of a thin, palish brown suspension of 2-aminonaphthalene-6(8)-sulfonic acid (salt) (pH 13.4). 868 parts of approximately 18% strength aqueous ammonia (about 75% of theory) are then distilled at atmospheric pressure up to a temperature at the top of 100° C. (bath temperature up to 150° C., cold trap as receiver). The ammonia distillate is slightly turbid due to xylene droplets and according to HPTLC contains no 2-aminonaphthalene (<3 ppm).

After replenishing with 77 parts of gaseous ammonia to 25%, 775 parts thereof are used for the next batch, about 170 parts are removed from the system.

The suspension (3600 parts, pH 13.4) runs in about 15 minutes from a dripping funnel into initially charged, externally cooled 1034 parts of approximately 30% strength hydrochloric acid (8.8 moles) (→pH 0.6). The temperature is then raised to the boil, and the sulfur dioxide is quantitatively expelled in about 2 hours by boiling. The sulfur dioxide is trapped in a mixture of 164 parts of water and 267 parts of 33% strength sodium hydroxide solution. This gives 572 parts of a 40% strength sodium hydrogen sulfite solution (2.2 moles corresponding to 93% of theory), which are used again for the next batch. This gives 4730 parts of a suspension which, according to the diazotization value, contains 6.1% by weight (287.5 parts) of 2-aminonaphthalene-6(8)-sulfonic acid (1.287 moles =85.8% of theory, based on 2-hydroxynaphthalene) and 3 ppm of 2-aminonaphthalene (HPTLC, scanner).

(c) The suspension thus obtained (according to diazotization value 4730 parts 6.1% strength =1.287 moles of 2-aminonaphthalene-6(8)-sulfonic acid) is brought at 70° C. with 314 parts of 33% strength sodium hydroxide solution to pH 7.0 and is treated with 0.3 part of a defoamer (fluorinated organic compound). 158 parts of acetic anhydride (1.54 moles) are then added with stirring in the course of 15 minutes.

During that time the pH decreases to 3.2 and the Brönner acid goes into solution. The acetylation is quantitative (DC and nitrosation). Isolation by means of salting out gives 277 parts of isomer-free 2-acetaminonaphthalene-6-sulfonic acid calculated at 100% (=1.04 moles corresponding to 81% of theory based on the diazotization value or 69.3% of theory based on 2-hydroxynaphthalene) with a purity of about 70% (acetyl determination and carbon analysis, molecular weight 265.3, HPTLC).

The 2-acetaminonaphthalene content is about 50 ppm (HPLC).

The mother liquor, in addition to the target product, also contains the isomeric 2-acetaminonaphthalene-8sulphonic acid (about 4 mol%) (HPTLC) and traces of 2-acetaminonaphthalene (<0.3 part).

We claim:

1. In a single-vessel process for preparing 2-acetaminonaphthalene-6-sulfonic acid of high purity by sulfonating 2-hydroxynaphthalene with concentrated sulfonic acid, converting the 2-hydroxynaphthalenesulfonic acid formed thereby with ammonia in the presence of ammonium hydrogensulfite into 2-aminonaphthalene-6-sulfonic acid (Bucherer reaction) and N-acetylating the said 2-aminonaphthalene-6-sulfonic acid to give 2-acetaminonaphthalene-6-sulfonic acid, the improvement which comprises:

after diluting the sulfonating melt with water, substantially removing any impurities still present in the resulting aqueous solution of 2-hydroxynaphthalene-6-sulfonic acid by clarification using active carbon.

2. In a single-vessel process for preparing 2-acetaminophthalene-6-sulfonic acid of high purity by sulfonating 2-hydroxynaphthalene with concentrated sulfuric acid, converting the 2-hydroxynaphthalenesulfonic acid formed thereby with ammonia in the presence of ammonium hydrogensulfite into 2-aminonaphthalene-6-sulfonic acid (Bucherer reaction and N-acetylating the said 2-aminonaphthalene-6-sulfonic acid to give 2 acetaminonaphthalene-6-sulfonic acid, the improvement which comprises:

after diluting the sulfonating melt with water, substantially removing any impurities still present in the resulting aqueous solution of 2-hydroxynaphthalene-6-sulfonic acid by extraction with toluene or xylene and clarification using active carbon.

3. A process as claimed in claim 2 wherein a said impurity which is removed is 2-hydroxynaphthalene.

* * * * *